US010625048B2

(12) United States Patent
Wada

(10) Patent No.: US 10,625,048 B2
(45) Date of Patent: Apr. 21, 2020

(54) INTRODUCER SHEATH

(71) Applicant: TERUMO KABUSHIKI KAISHA, Shibuya-ku, Tokyo (JP)

(72) Inventor: Satoshi Wada, Shizuoka (JP)

(73) Assignee: TERUMO KABUSHIKI KAISHA, Shibuya-ku, Tokyo (JP)

( * ) Notice: Subject to any disclaimer, the term of this patent is extended or adjusted under 35 U.S.C. 154(b) by 33 days.

(21) Appl. No.: 15/680,558

(22) Filed: Aug. 18, 2017

(65) Prior Publication Data
US 2018/0056036 A1 Mar. 1, 2018

(30) Foreign Application Priority Data
Sep. 1, 2016 (JP) .................. 2016-171041

(51) Int. Cl.
*A61M 25/00* (2006.01)
*A61M 25/06* (2006.01)
(Continued)

(52) U.S. Cl.
CPC .... *A61M 25/0045* (2013.01); *A61M 25/0097* (2013.01); *A61M 25/0662* (2013.01);
(Continued)

(58) Field of Classification Search
CPC .. A61M 2025/0062; A61M 2025/0048; A61M 2025/0057; A61M 2025/0681;
(Continued)

(56) References Cited

U.S. PATENT DOCUMENTS 4,430,081 A * 2/1984 Timmermans .... A61M 39/0606
251/149.1
4,596,563 A * 6/1986 Pande ............... A61M 25/0045
604/264
(Continued)

FOREIGN PATENT DOCUMENTS

JP H06-510460 A 11/1994
JP H07-506513 A 7/1995
(Continued)

OTHER PUBLICATIONS

Notice of Reasons for Refusal issued by the Japanese Patent Office in corresponding Japanese Patent Application No. 2016-171041 dated Jan. 28, 2020 (9 pages including partial English translation).

*Primary Examiner* — Bhisma Mehta
*Assistant Examiner* — Nilay J Shah
(74) *Attorney, Agent, or Firm* — Buchanan Ingersoll & Rooney PC

(57) ABSTRACT

An introducer sheath is disclosed capable of reducing a physical burden on a patient by shortening a time necessary for hemostasis at an introduction part after removing the introducer sheath percutaneously introduced into a body lumen. The introducer sheath includes a catheter main body, which is percutaneously introduced into a body lumen, a hub, which is connected to a proximal side of the catheter main body, and a tube member which includes a thrombus inducing material M. The tube member is disposed at a proximal side of an outer surface of the catheter main body.

20 Claims, 6 Drawing Sheets

(51) Int. Cl.
*A61M 29/02* (2006.01)
*A61M 39/06* (2006.01)

(52) U.S. Cl.
CPC ............ *A61M 29/02* (2013.01); *A61M 39/06* (2013.01); *A61M 2025/0046* (2013.01); *A61M 2025/0098* (2013.01); *A61M 2025/0681* (2013.01); *A61M 2205/584* (2013.01)

(58) Field of Classification Search
CPC .............. A61M 25/00; A61M 25/0062; A61M 25/005; A61M 25/0097; A61M 25/0045
See application file for complete search history.

(56) References Cited

U.S. PATENT DOCUMENTS

| | | | |
|---|---|---|---|
| 4,897,077 A * | 1/1990 | Cicciu | A61M 25/06 600/18 |
| 5,254,105 A | 10/1993 | Haaga | |
| 5,290,310 A | 3/1994 | Makower et al. | |
| 5,324,306 A | 6/1994 | Makower et al. | |
| 5,399,352 A * | 3/1995 | Hanson | A61F 2/06 424/423 |
| 6,090,072 A * | 7/2000 | Kratoska | A61B 17/3439 604/164.01 |
| 7,811,257 B2 * | 10/2010 | Saab | A61M 39/0247 604/175 |
| 2013/0023734 A1 | 1/2013 | Okamura | |
| 2014/0058443 A1 * | 2/2014 | Zhu | A61B 17/0057 606/215 |
| 2015/0032056 A1 * | 1/2015 | Okamura | A61M 25/0662 604/164.1 |
| 2015/0094795 A1 * | 4/2015 | Ginn | A61F 2/962 623/1.12 |
| 2016/0199619 A1 | 7/2016 | Okamura | |

FOREIGN PATENT DOCUMENTS

| | | |
|---|---|---|
| KR | 10-2014-0101502 A | 8/2014 |
| WO | WO 2011/122488 A1 | 10/2011 |
| WO | 2012/172861 A1 | 12/2012 |

* cited by examiner

INTRODUCER SHEATH

CROSS-REFERENCES TO RELATED APPLICATIONS

This application claims priority to Japanese Application No. 2016-171041 filed on Sep. 1, 2016, the entire content of which is incorporated herein by reference.

TECHNICAL FIELD

The present disclosure relates to an introducer sheath which is used in an introducer assembly corresponding to a medical instrument.

BACKGROUND DISCUSSION

In a medical field, a technique of percutaneously introducing various catheters into a living body is performed. In such a technique, an introducer sheath including a catheter main body percutaneously introduced into a body lumen and a hub connected to a proximal side of the catheter main body is used (for example, see WO 2011/122488). The introducer sheath forms an access path connecting the inside and the outside of the living body when the catheter main body is percutaneously introduced into the body lumen.

The introducer sheath is removed after the above-described technique (hereinafter, a desired procedure) of percutaneously introducing various catheters into a living body. After the introducer sheath is removed, there can be a need to perform hemostasis at a portion (hereinafter, an introduction part) into which the introducer sheath is introduced.

As a hemostasis method, a hemostasis method of pressing the introduction part by using, for example, a balloon or the like inflated by a fluid injected thereto is widely used. However, a patient may feel a physical burden when the introduction part is pressed for hemostasis of the introduction part for a long period of time. For that reason, a technique of reducing a physical burden on a patient requiring the hemostasis of the introduction part has been demanded.

SUMMARY

An introducer sheath is disclosed, which is capable of reducing a physical burden on a patient by shortening a time necessary for hemostasis at an introduction part after removing the introducer sheath percutaneously introduced into a body lumen.

In accordance with an exemplary embodiment, the introducer sheath according to the disclosure includes: a catheter main body, which is percutaneously introduced into a body lumen; a hub, which is connected to a proximal side of the catheter main body; and a tube member that includes a thrombus inducing material. Then, the tube member is disposed at a proximal side of the outer surface of the catheter main body.

According to the introducer sheath of the disclosure, the thrombus inducing material can be indwelled in the introduction part by inserting the proximal side of the catheter main body into the introduction part during a desired procedure. For that reason, the formation of the thrombus at the introduction part can be promoted before removing the introducer sheath. Thus, a physical burden on a patient can be reduced by shortening a time necessary for hemostasis at the introduction part after removing the introducer sheath percutaneously introduced into the body lumen.

In accordance with an exemplary embodiment, a method is disclosed of indwelling an introducer sheath in a body lumen, comprising: puncturing a body lumen in which an introducer sheath needs to be indwelled; and introducing an introducer sheath into a puncture site of the body lumen, the introducer sheath including a catheter main body having a portion provided with a thrombus inducing material and a hub, which is connected to a proximal side of the catheter main body, and wherein the catheter main body is indwelled in the body lumen while a part of the portion provided with the thrombus inducing material is inserted into the body lumen through the puncture site.

In accordance with an exemplary embodiment, a method is disclosed of treating a lesion area of a body lumen, comprising: introducing an introducer sheath into a puncture site of a body lumen, the introducer sheath including a catheter main body which has a portion provided with a thrombus inducing material and a hub which is connected to a proximal side of the catheter main body; indwelling the catheter main body in the body lumen while disposing a portion provided with the thrombus inducing material at the puncture site; and introducing a treatment instrument for treating the lesion area into the body lumen through the introducer sheath while a portion provided with the thrombus inducing material in the catheter main body is disposed at the puncture site.

DETAILED DESCRIPTION

Hereinafter, an introducer assembly 10 according to a first exemplary embodiment will be described with reference to the drawings.

FIGS. 1 to 3B are diagrams illustrating components of an introducer assembly 10 and FIGS. 4A to 5B are diagrams provided for a description of a treatment method using an introducer sheath 100.

Figure 2:
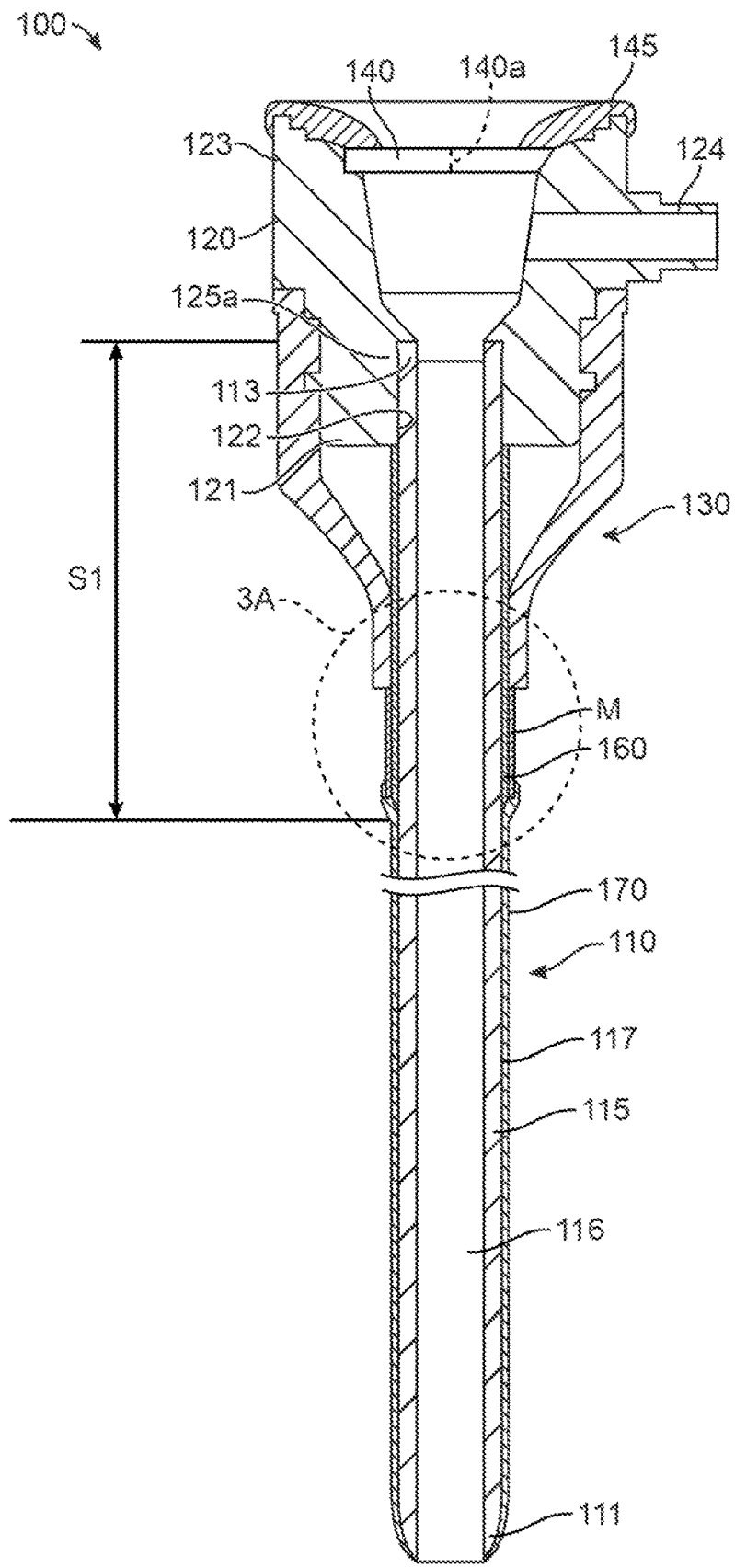
FIG. 2 is a cross-sectional view of an introducer sheath according to the embodiment.

Referring to FIG. 2, in the specification, a side in which a hub (hub) 120 is disposed in the introducer sheath 100 (an upper side in FIG. 2) will be referred to as a "proximal side". A side which is opposite to the proximal side in the introducer sheath 100 and is introduced into a body lumen R (a lower side in FIG. 2) will be referred to as a "distal side". Further, a direction in which the introducer sheath 100 extends (a vertical direction in FIG. 2) will be referred to as an "axial direction". Further, a "distal area" means a distal end (a most distal end) and a predetermined range including the periphery thereof and a "proximal portion" means a proximal end (a most proximal end) and a predetermined range including the periphery thereof.

Figure 5A:
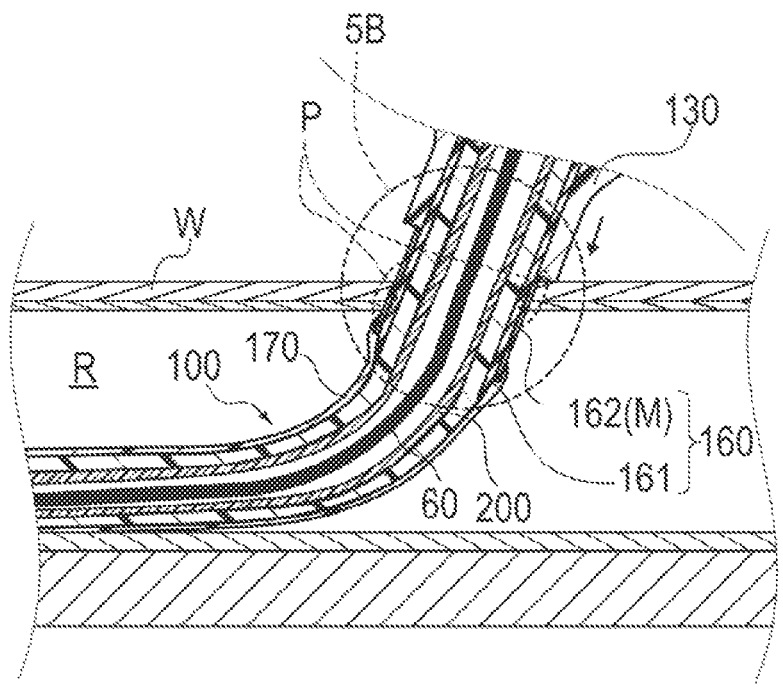
FIG. 5A is a schematic cross-sectional view illustrating a state where a thrombus inducing material is indwelled in an introduction part.
Figure 5B:
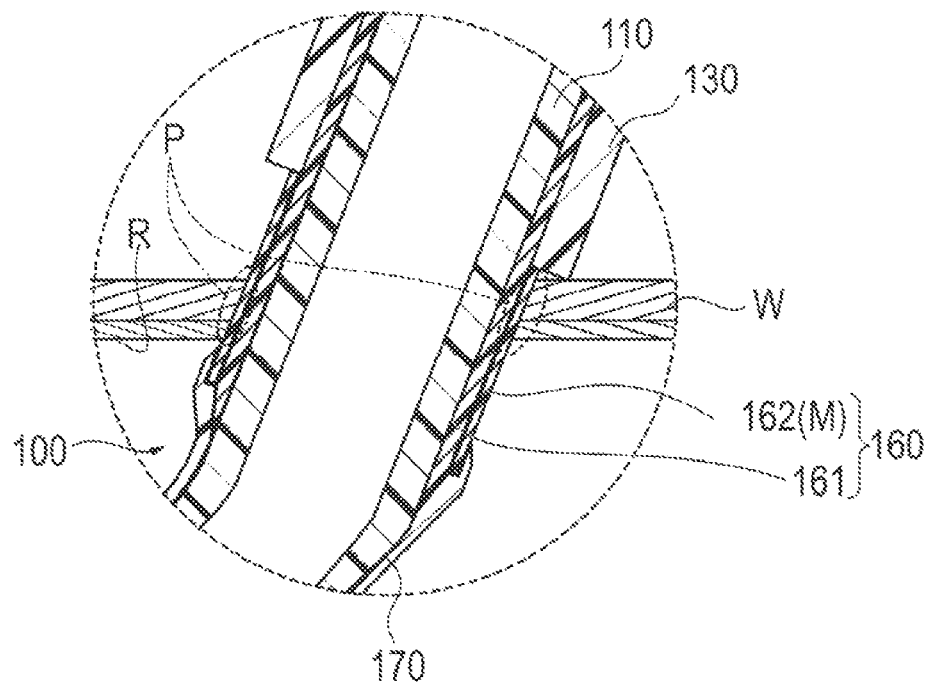
FIG. 5B is an enlarged view of a dashed line portion 5B of FIG. 5A in a state where the thrombus inducing material is indwelled in the introduction part.

Further, referring to FIGS. 5A and 5B, a part P of a body tissue W in which the introducer sheath 100 is percutaneously inserted into the body lumen R will be referred to as an "introduction part".

Figure 1:
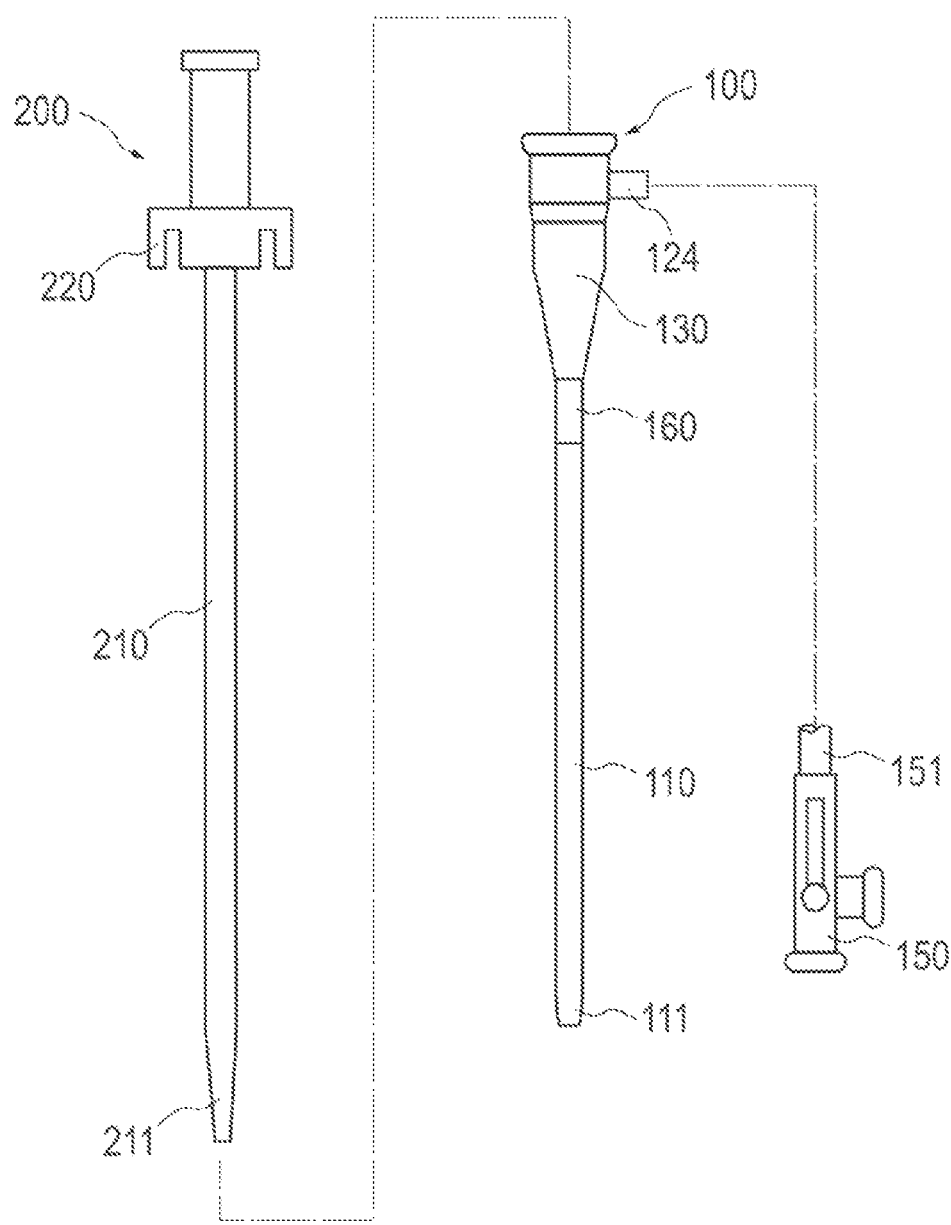
FIG. 1 is a diagram illustrating an introducer assembly according to an embodiment.

As illustrated in FIG. 1, the introducer assembly 10 according to the embodiment includes the introducer sheath 100 and a dilator 200. Hereinafter, the introducer sheath 100 and the dilator 200 will be described in detail.

The introducer sheath 100 is indwelled inside the body lumen R, for example, a blood vessel and is used to insert, for example, a mechanism such as a catheter and a guide wire into a lumen 116 and to introduce the mechanism into the body lumen R. By using a guide wire introduced into the body lumen R, for example, a procedure such as percutaneous transluminal coronary angioplasty (PTCA/PCI) (hereinafter, referred to as a desired procedure) can be performed. As an approach to percutaneous transluminal coronary angioplasty, a TFI (Trans Femoral Intervention) which introduces the introducer sheath from the foot and a TRI (Trans Radial Intervention) which introduces the introducer sheath from the arm are known.

The introducer sheath 100 can include, as illustrated in FIG. 2, a catheter main body 110 which is percutaneously introduced into the body lumen R, the hub 120 which is connected to the proximal side of the catheter main body 110, and a tube member (or tubular member) 160 which includes a thrombus inducing material M. Then, the tube member 160 is disposed at the proximal side of an outer surface 117 of the catheter main body 110.

In accordance with an exemplary embodiment, the catheter main body 110 is formed as a substantially cylindrical tubular member in which the lumen 116 extends therein. The catheter main body 110 can include, as illustrated in FIG. 2, a tapered distal area 111, a main body portion 115, which is positioned at the proximal side of the distal area 111, and a proximal portion 113, which is positioned at the proximal side of the main body portion 115 and is connected to the hub 120.

A material of forming the catheter main body 110 is not particularly limited and, for example, polymeric materials such as polyolefin (for example, polyethylene, polypropylene, polybutene, ethylene-propylene copolymer, ethylene-vinyl acetate copolymer, ionomer, or a mixture of two or more thereof), polyolefin elastomer, crosslinked polyolefin, polyvinyl chloride, polyamide, polyamide elastomer, polyester, polyester elastomer, polyurethane, polyurethane elastomer, fluororesin, polycarbonate, polystyrene, polyacetal, polyimide, polyether imide, polyether ether ketone or a mixture thereof can be used.

In accordance with an exemplary embodiment, a hydrophilic lubrication layer 170 which applies surface lubricity in a wet state can be disposed on the outer surface 117 of the catheter main body 110.

A material of forming the hydrophilic lubrication layer 170 is a material exhibiting hydrophilicity and swellability when contacting an aqueous solvent. A layer including such a material exhibits hydrophilicity and lubricity (surface lubricity) when the catheter main body 110 is inserted into a body. For that reason, the catheter main body 110 on which the hydrophilic lubrication layer is disposed can be smoothly inserted into a body and thus the operability of an operator can be improved. Further, for example, when the catheter main body 110 is inserted into a body lumen such as a blood vessel, damage of a tissue is reduced due to hydrophilicity and lubricity (surface lubricity) and thus a burden on a patient can be reduced.

A material of forming the hydrophilic lubrication layer 170 is not particularly limited as long as the material exhibits hydrophilicity and swellability when contacting an aqueous solvent and a known material can be used. Specific examples thereof can include a copolymer of an epoxy group-containing monomer such as glycidyl acrylate, glycidyl methacrylate, 3,4-epoxycyclohexylmethyl acrylate, 3,4-epoxycyclohexylmethyl methacrylate, β-methylglycidyl methacrylate, or allyl glycidyl ether and a hydrophilic monomer such as N-methylacrylamide, N,N-dimethylacrylamide, or acrylamide; a (co)polymer composed of the above-described hydrophilic monomer; a cellulose-based high-molecular substance such as hydroxypropyl cellulose or carboxymethyl cellulose; polysaccharides, polyvinyl alcohol, a methyl vinyl ether-maleic anhydride copolymer, a water-soluble polyamide, poly(2-hydroxyethyl(meth)acrylate), polyethyleneglycol, polyacrylamide, polyvinylpyrrolidone, and a copolymer of polyvinylpyrrolidone described in U.S. Pat. No. 4,100,309 and JP-A-59-19582 and polyurethane. These materials forming the hydrophilic lubrication layer 170 may be used alone or in the form of a mixture of two or more.

As illustrated in FIG. 2, the hub 120 is provided with a lumen 122 to which the proximal portion 113 of the catheter main body 110 can be fixed and a side port 124 which communicates with the lumen 122.

In accordance with an exemplary embodiment, one end of a flexible tube 151 (see FIG. 1) is liquid-tightly connected to the side port 124. For example, a three-way stopcock 150 can be attached to the other end of the tube 151. For example, a liquid such as a physiological salt solution can be injected from the port of the three-way stopcock 150 into the lumen 116 of the catheter main body 110 through the tube 151. The tube 151 can be formed as, for example, a known tube formed of polyvinyl chloride.

A material of forming the hub 120 is not particularly limited and a hard material such as a hard resin is desirable. As a detailed example of the hard resin, for example, polyolefin such as polyethylene and polypropylene, polyamide, polycarbonate, polystyrene, and the like can be exemplified.

A hemostatic valve 140 which prevents blood flowing into the catheter main body 110 from leaking to the outside is attached to a proximal portion 123 of the hub 120. The hemostatic valve 140 is formed as an elastic member provided with a cross cut 140a allowing a dilator main body 210 to be inserted therethrough. In accordance with an exemplary embodiment, the hemostatic valve 140 is formed in a substantially elliptical film shape (disc shape) and is liquid-tightly fixed to the hub 120 by fitting a predetermined cap 145.

A material of forming the hemostatic valve 140 is not particularly limited and, for example, silicone rubber, latex rubber, butyl rubber, isoprene rubber, and the like which are elastic members can be exemplified.

In accordance with an exemplary embodiment, the proximal portion 113 of the catheter main body 110 is fixed to an interlock portion 125a of the hub 120. The interlock portion 125a between the hub 120 and the proximal portion 113 of the catheter main body 110 can be fixed by, for example, an adhesive.

As illustrated in FIG. 2, a strain relief 130 is externally fitted to the catheter main body 110 and the hub 120. The strain relief 130 covers a distal portion 121 of the hub 120 and surrounds a predetermined range of the proximal side of the catheter main body 110.

Since the introducer sheath 100 includes the strain relief 130, the kink of the introducer sheath 100 at the proximal side when the introducer sheath 100 is introduced or indwelled into the body lumen R can be prevented.

A material of forming the strain relief 130 is not particularly limited and, for example, natural rubber, silicone resin, and the like can be exemplified.

As illustrated in FIG. 1, the dilator 200 includes the dilator main body 210 which is formed as a tubular body insertable into the catheter main body 110 and a dilator hub 220 which is connectable to the hub 120.

In accordance with an exemplary embodiment, the dilator 200 can be used to prevent the bending of the catheter main body 110 or to widen the perforation of the skin when the catheter main body 110 of the introducer sheath 100 is inserted into the body lumen R.

When the dilator main body 210 is inserted through the catheter main body 110, the distal area 211 protrudes from the distal area 111 of the catheter main body 110. A distal area 211 of the dilator main body 210 is formed in a tapered shape, which is tapered toward the distal side.

A material of forming the dilator main body 210 is not particularly limited and a material which is used conventionally as the dilator main body 210 can be used. Specifically, for example, polyolefin such as polypropylene (PP) and polyethylene (PE), polyester such as nylon and polyethylene terephthalate (PET), fluorinated polymer such as polyvinylidene fluoride (PVDF) and tetrafluoroethylene hexafluoropropylene copolymer (FEP) can be exemplified.

A material of forming the dilator hub 220 is not particularly limited and a hard material such as a hard resin is desirable. As a detailed example of the hard resin, for example, polyolefin such as polyethylene and polypropylene, polyamide, polycarbonate, polystyrene, and the like can be exemplified.

Figure 3A:
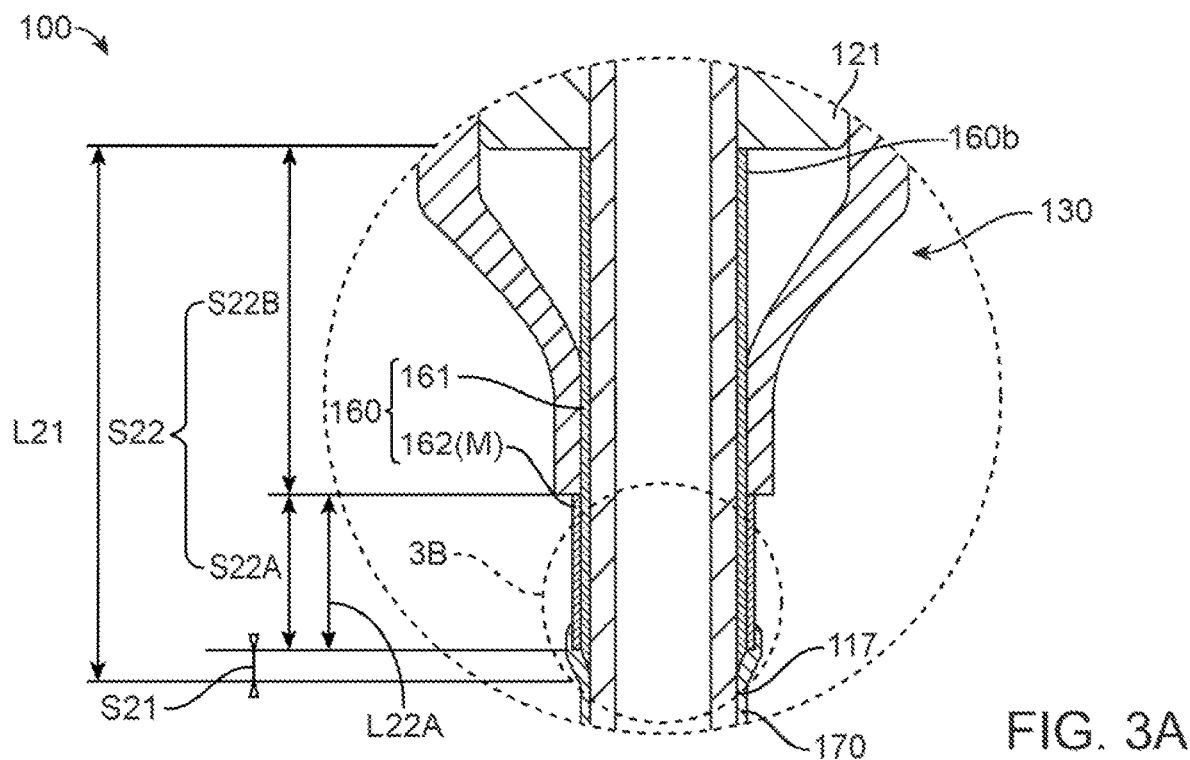
FIG. 3A is an enlarged view of a dashed line portion 3A of FIG. 2 according to an exemplary embodiment.
Figure 3B:
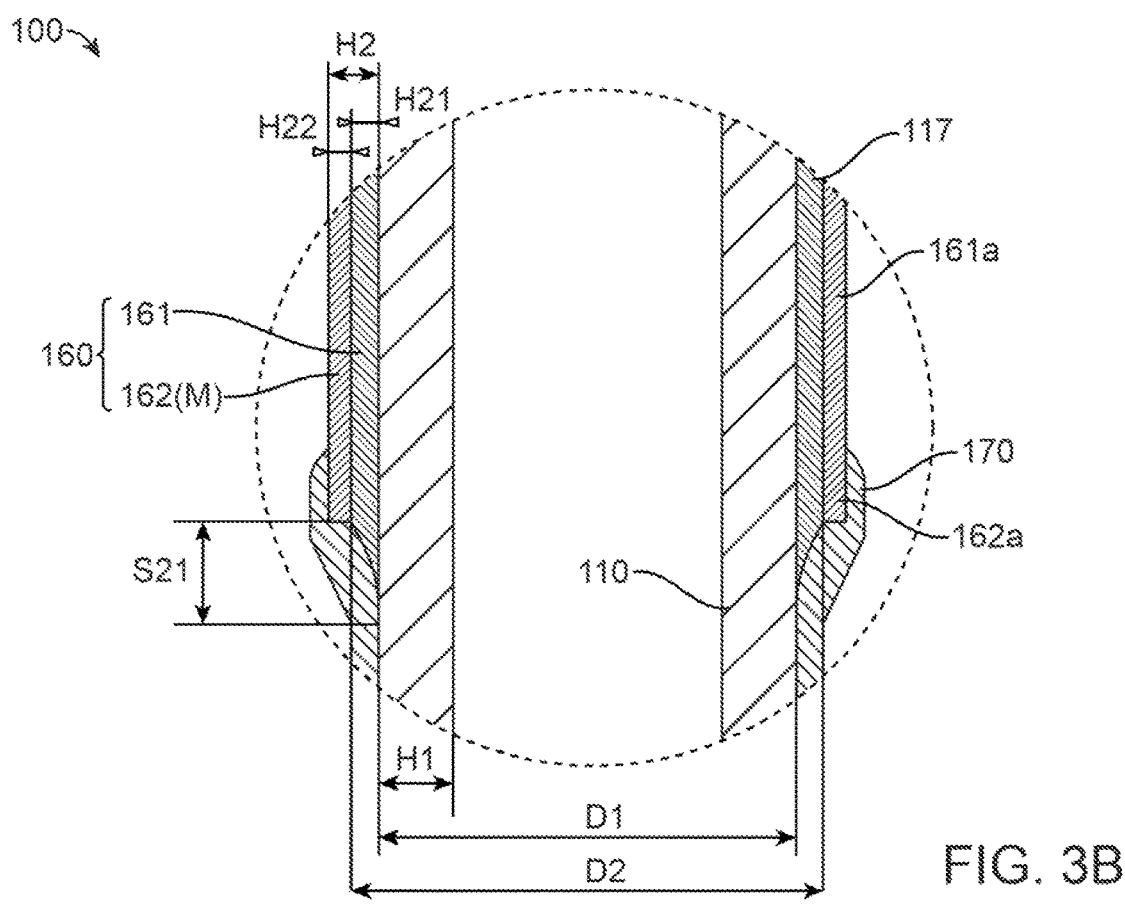
FIG. 3B is an enlarged view of a dashed line portion 3B of FIG. 3A according to an exemplary embodiment.
Figure 4A:
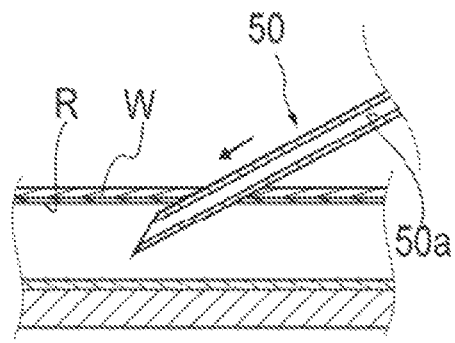
FIG. 4A is a schematic cross-sectional view illustrating a treatment method using the introducer sheath according to the embodiment and illustrating a state of puncturing using an introduction needle.
Figure 4B:
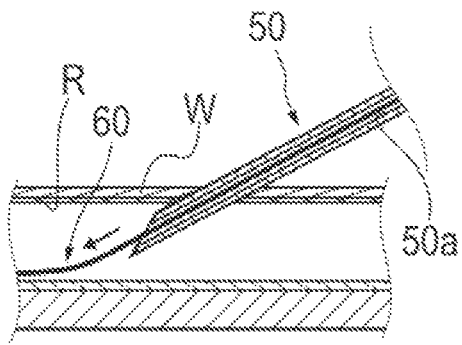
FIG. 4B is a schematic cross-sectional view illustrating a treatment method using the introducer sheath according to the embodiment and illustrating a state of inserting a guide wire into a body lumen.
Figure 4C:
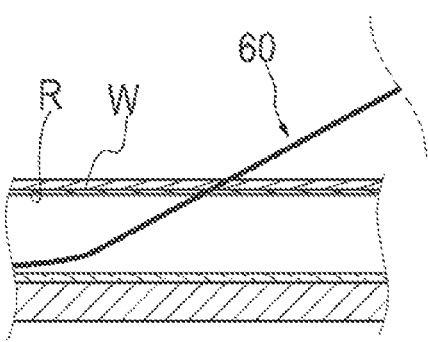
FIG. 4C is a schematic cross-sectional view illustrating a treatment method using the introducer sheath according to the embodiment and illustrating a state where the guide wire is indwelled in the body lumen.
Figure 4D:
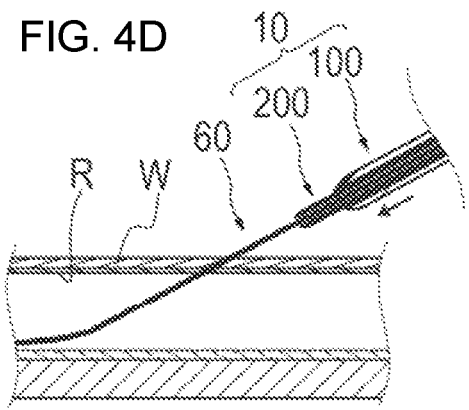
FIGS. 4D and 4E are schematic cross-sectional views illustrating a treatment method using the introducer sheath according to the embodiment and illustrating a state of puncturing using an introducer assembly.
Figure 4E:
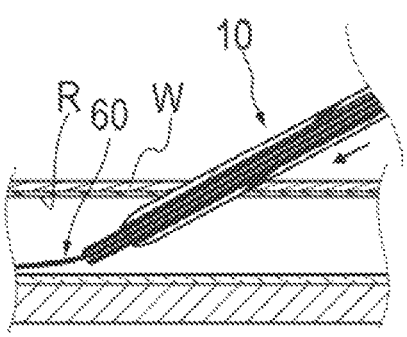

Referring to FIGS. 2, 3A, and 3B, the thrombus inducing material M, the strain relief 130, and the tube member 160 will be described in detail.

The thrombus inducing material M is disposed at the proximal side of the outer surface 117 of the catheter main body 110. The thrombus inducing material M promotes the formation of thrombus at the introduction part P (see FIGS. 5A and 5B). The thrombus inducing material M promotes the formation of the thrombus at the introduction part P by collecting a biological material such as platelet contributing to the formation of the thrombus in the vicinity of, for example, the introduction part P during a desired procedure.

In accordance with an exemplary embodiment, in the catheter main body 110, the thrombus inducing material M is disposed at the proximal side of the outer surface 117. For this reason, an operator can indwell the thrombus inducing material M in the introduction part P by inserting the proximal side of the catheter main body 110 into the introduction part P during a desired procedure. For that reason, it is possible to promote the formation of the thrombus in the introduction part P before removing the introducer sheath 100 from the body lumen R. As a result, it is possible to shorten a time necessary for hemostasis at the introduction part P after the introducer sheath 100 percutaneously introduced into the body lumen R is removed from the body lumen R.

More specifically, for example, the following method is considered as a method of indwelling the thrombus inducing material M in the introduction part P during a desired procedure. In accordance with an exemplary embodiment, a method is considered which holds the thrombus inducing material M in the lumen of the tubular member, inserts the tubular member into the introduction part P while being independent from or interlocked with an operation of inserting the catheter main body 110 into the introduction part P, releases the holding of the thrombus inducing material M at the tubular member inserted into the introduction part P, and indwells the thrombus inducing material M in the introduction part P. The releasing of the holding of the thrombus inducing material M in the tubular member is performed according to, for example, a method of extruding the thrombus inducing material M from the lumen of the tubular member.

However, in the case of the method of indwelling the thrombus inducing material M at the introduction part P using the tubular member, the introduction part P is widened since the tubular member is inserted into the introduction part P along with the catheter main body 110. Since further bleeding occurs, there is a concern that hemostasis can be difficult. Further, since there can be a need to perform an operation of releasing the holding of the thrombus inducing material M in the tubular member in order to indwell the thrombus inducing material M in the introduction part P, a sequence of indwelling the thrombus inducing material M in the introduction part P becomes complex.

According to the introducer sheath 100 of the embodiment, the introduction part P can be prevented from being excessively widened when the thrombus inducing material M is indwelled in the introduction part P and it is not necessary to perform an operation of releasing the holding of the thrombus inducing material M in the above-described tubular member. For that reason, it is possible to promote hemostasis at the introduction part P with a simple structure and sequence.

The thrombus inducing material M is not particularly limited as long as the formation of the thrombus in the introduction part P can be promoted and, for example, collagen, high molecular weight vWF factor, and the like can be used.

The tube member 160 is disposed at the proximal side of the outer surface 117 of the catheter main body 110. Further, the tube member 160 includes the thrombus inducing material M.

For this reason, in the introducer sheath 100, the outer diameter of the proximal portion provided with the thrombus inducing material M indwelled in the introduction part P increases by a thickness H2 of the tube member 160 while the outer diameter of the distal portion passing through the introduction part P is maintained. Accordingly, the proximal portion provided with the thrombus inducing material M can further adhere to the introduction part P while the passage of the distal portion of the introducer sheath 100 through the introduction part P is allowed without excessively widening the introduction part P. For that reason, the introducer sheath 100 can prevent a positional deviation of a portion provided with the thrombus inducing material M in the introducer sheath 100 from the introduction part P without further bleeding at the introduction part P and allow the thrombus inducing material M to more reliably contact the introduction part P. As a result, it is possible to more reliably shorten a time necessary for hemostasis at the introduction part P using the introducer sheath 100. Further, since a positional deviation of the portion provided with the thrombus inducing material M in the introducer sheath 100 from the introduction part P is difficult, the thrombus inducing material M can be easily indwelled in the introduction part P for a long period of time. For that reason, this is particularly effective when a desired procedure is performed for a long period of time.

Note that an adhering state between the introduction part P and the portion provided with the thrombus inducing material M in the introducer sheath 100 changes depending on the outer diameter of the portion provided with the thrombus inducing material M. In order to cause the introduction part P to appropriately adhere to the portion provided with the thrombus inducing material M without excessively widening the introduction part P, it can be desirable to finely adjust the outer diameter of the portion provided with the thrombus inducing material M. According to a configuration in which the tube member 160 having the thrombus inducing material M is disposed at the proximal side of the outer surface 117 of the catheter main body 110, it is possible to easily and finely adjust the outer diameter of the portion provided with the thrombus inducing material M by adjusting the thickness H2 of the tube member 160. For that reason, the introduction part P can appropriately adhere to the portion provided with the thrombus inducing material M without excessively widening the introduction part P.

In accordance with an exemplary embodiment, the strain relief 130 covers a part of the tube member 160.

Accordingly, the rigidity of the introducer sheath 100 gradually increases in order of a portion 110P1 only at the catheter main body 110, a portion 110P2 provided with the tube member 160 in the catheter main body 110, and a portion 110P3 provided with the tube member 160 and the strain relief 130 in the catheter main body 110 in a direction from the distal side to the proximal side of the catheter main body 110. For that reason, the kink at the proximal side of the introducer sheath 100 can be more effectively prevented.

In accordance with an exemplary embodiment, the tube member 160 can include a main body portion 161 and a medicine portion 162, which is disposed on an outer surface 161a of the main body portion 161 and has the thrombus inducing material M.

In accordance with an exemplary embodiment, the main body portion 161 of the tube member 160 has a substantially cylindrical shape. In the main body portion 161 of the tube member 160, a proximal portion 160b contacts the distal portion 121 of the hub 120 and extends from the distal portion 121 of the hub 120 to have a predetermined length in a direction from the proximal side to the distal side of the introducer sheath 100. A length L21 of the main body portion 161 of the tube member 160 is not particularly limited and can be arbitrarily set to, for example, a range of 5 mm to 100 mm.

Note that the proximal portion 160b of the main body portion 161 of the tube member 160 may extend to the proximal portion 113 of the catheter main body 110. In that case, the proximal portion 160b of the main body portion 161 of the tube member 160 or the proximal portion 160b of the main body portion 161 of the tube member 160 and the proximal portion 113 of the catheter main body 110 are fixed to the interlock portion 125a of the hub 120.

The size of an outer diameter D1 (see FIG. 3B) of the catheter main body 110 is not particularly limited and can be arbitrarily set to, for example, a range of 1 mm to 3 mm. An outer diameter D2 of the main body portion 161 of the tube member 160 is not particularly limited and can be arbitrarily set to, for example, a range of 1.1 mm to 4.5 mm.

In accordance with an exemplary embodiment, the medicine portion 162 has a predetermined thickness H22 and is disposed on the outer surface 161a of the main body portion 161 of the tube member 160. The medicine portion 162 is disposed in the entire circumference in a predetermined range of the outer surface 161a of the main body portion 161 of the tube member 160.

The main body portion 161 of the tube member 160 can include a distal area S21 and a proximal area S22, which is positioned at the proximal side in relation to the distal area S21. The proximal area S22 includes an area S22A, which is not covered by the strain relief 130 and an area S22B, which is covered by the strain relief 130. The medicine portion 162 is disposed on the area S22A, which is not covered by the strain relief 130 in the outer surface 161a of the main body portion 161 of the tube member 160. Note that the medicine portion 162 may be disposed on the area S22A not covered by the strain relief 130 and the area S22B covered by the strain relief 130 in the outer surface 161a of the main body portion 161 of the tube member 160.

The thickness H2 of the tube member 160 is smaller than the thickness H1 of the catheter main body 110. Then, a material of the tube member 160 is harder than a material of the catheter main body 110.

Accordingly, the rigidity of the tube member 160 can be increased without increasing the outer diameter of the portion provided with the tube member 160 in the introducer sheath 100 more than necessarily. Accordingly, the tube member 160 can be prevented from being rolled up toward the proximal side of the catheter main body 110 due to a resistance applied from the body tissue W to the distal side of the tube member 160 when the tube member 160 is introduced into the introduction part P.

Further, since the rigidity of the tube member 160 increases, the rigidity of the portion provided with the tube member 160 in the introducer sheath 100 increases. As described above, the strain relief 130 according to the embodiment covers a part of the tube member 160. For that reason, since the rigidity of the portion provided with the tube member 160 increases, the following operation and effect can be obtained. In accordance with an exemplary embodiment, the rigidity of the introducer sheath 100 more smoothly and gradually increases in order of the portion 110P1 only at the catheter main body 110, the portion 110P2 provided with the tube member 160 in the catheter main body 110, and the portion 110P3 provided with the tube member 160 and the strain relief 130 in the catheter main body 110 in a direction from the distal side to the proximal side of the catheter main body 110. For that reason, the kink at the proximal side of the introducer sheath 100 can be more effectively prevented. Further, since the outer diameter of the portion provided with the tube member 160 in the introducer sheath 100 does not increase more than necessarily as described above, the insertability into the introduction part P is not damaged.

The thickness H1 of the catheter main body 110 is not particularly limited and can be set to, for example, a range of 0.1 mm to 0.5 mm.

The thickness H2 of the tube member 160 is not particularly limited as long as the thickness is smaller than the thickness H1 of the catheter main body 110. In the embodiment, the thickness H2 of the tube member 160 is a sum of a thickness H21 of the main body portion 161 and the thickness H22 of the medicine portion 162. That is, in the embodiment, a sum of the thickness H21 of the main body portion 161 and the thickness H22 of the medicine portion 162 of the tube member 160 is smaller than the thickness H1 of the catheter main body 110. The thickness H21 of the main body portion 161 of the tube member 160 is not particularly limited and can be arbitrarily set to, for example, a range of 0.05 mm to 0.2 mm. The thickness H22 of the medicine portion 162 is not particularly limited and can be arbitrarily set to, for example, a range of 0.1 mm to 0.5 mm.

A material of the tube member 160 is not particularly limited as long as the material is harder than a material of the catheter main body 110. When the material of the tube member 160 includes a plurality of materials, a material which gives a rigidity to the tube member 160 among the plurality of materials may be harder than the material of the catheter main body 110. In the embodiment, a material of the main body portion 161 of the tube member 160 is harder than the material of the catheter main body 110.

The material of the main body portion 161 of the tube member 160 is not particularly limited as long as the material is harder than the material of the catheter main body 110. For example, when polyethylene or polypropylene is used as the material of forming the catheter main body 110, polycarbonate and polyether ether ketone (PEEK) can be used as the material of forming the tube member 160. Further, low-density polyethylene may be used as the material of forming the catheter main body 110 and high-density polyethylene may be used as the material of forming the tube member 160.

In accordance with an exemplary embodiment, the distal area S21 of the main body portion 161 of the tube member 160 is inclined toward the outer surface 117 of the catheter main body 110. Specifically, the distal area S21 of the main body portion 161 of the tube member 160 is formed so that the outer periphery of the distal area S21 decreases in a direction from the proximal side to the distal side of the distal area S21.

At the time of introducing the tube member 160 into the introduction part P, the distal area S21 first contacting the body tissue W in the tube member 160 receives a large resistance from the body tissue W. For that reason, since the distal area S21 of the tube member 160 is inclined toward the outer surface 117 of the catheter main body 110, a resistance applied from the body tissue W to the distal area S21 of the tube member 160 when the tube member 160 is introduced into the introduction part P can be reduced. For that reason, the insertability of the tube member 160 into the introduction part P can be improved.

In accordance with an exemplary embodiment, a color of the tube member 160 can be different from a color of the catheter main body 110. Accordingly, an area in which the thrombus inducing material M is disposed in the catheter main body 110 can be more accurately recognized. For that reason, the tube member 160 can be more reliably inserted into the introduction part P.

A color of the catheter main body 110 is not particularly limited and is yellow in the embodiment. A color of the tube member 160 is not particularly limited and may be, for example, white.

A coloring method of the tube member 160 is not particularly limited and a known method can be used. For example, the tube member 160 can be colored by mixing a known colorant in the material of forming the tube member 160.

The hydrophilic lubrication layer 170 is partially disposed on the outer surface 117 of the catheter main body 110. In accordance with an exemplary embodiment, the catheter main body 110 can include an area S1 without the hydrophilic lubrication layer 170. In the embodiment, the area S1 without the hydrophilic lubrication layer 170 is set to the proximal side of the catheter main body 110.

The tube member 160 is disposed on the area S1 of the catheter main body 110 without the hydrophilic lubrication layer 170. Accordingly, the relative slip between the catheter main body 110 and the tube member 160 through the hydrophilic lubrication layer 170 can be prevented. For that reason, a relative positional deviation between the catheter main body 110 and the tube member 160 when the tube member 160 is inserted into the introduction part P can also be prevented. For this reason, the insertability of the tube member 160 into the introduction part P can be improved.

The hydrophilic lubrication layer 170 covers the distal area S21 of the tube member 160. Accordingly, a resistance applied from the body tissue W to the distal area S21 of the tube member 160 when the tube member 160 is introduced into the introduction part P can be further reduced. For that reason, the insertability of the tube member 160 into the introduction part P can be further improved.

In the embodiment, the hydrophilic lubrication layer 170 covers a part of the distal portion 162a of the medicine portion 162. For that reason, the hydrophilic lubrication layer 170 can help prevent the medicine portion 162 from being separated from the tube member 160 when the tube member 160 is introduced into the introduction part P.

Next, a treatment method using the introducer sheath 100 according to the embodiment will be described.

The treatment method using the introducer sheath 100 according to the embodiment includes a step of indwelling the introducer sheath 100, a step of performing a desired procedure, and a step of removing the introducer sheath 100. Then, the step of indwelling the introducer sheath 100 includes a step of indwelling the thrombus inducing material M in the introduction part P.

Referring to FIGS. 4A to 4E, in the step of indwelling the introducer sheath 100, the body lumen R indwelling the introducer sheath 100 is punctured by an introduction needle 50 (see FIG. 4A), the guide wire 60 is inserted into the body lumen R through a lumen 50a of the introduction needle 50 (see FIG. 4B), the introduction needle 50 is removed from the body lumen R while the guide wire 60 is indwelled in the body lumen R, the guide wire 60 is indwelled in the body lumen R (see FIG. 4C), the dilator 200 is allowed to follow the guide wire 60 indwelled in the body lumen R, a puncturing is performed by the introducer assembly 10 (see FIGS. 4D and 4E), and the guide wire 60 and the dilator 200 are removed from the introducer sheath 100 while the introducer sheath 100 is indwelled in the body lumen R.

Referring to FIGS. 5A and 5B, the step of indwelling the introducer sheath 100 includes a step of indwelling the thrombus inducing material M in the introduction part P.

In the step of indwelling the thrombus inducing material M in the introduction part P, the tube member 160 having the thrombus inducing material M and disposed at the proximal side of the outer surface 117 of the catheter main body 110 is inserted into the introduction part P (see FIG. 5A) and the tube member 160 is indwelled in the introduction part P (see FIG. 5B) at the time of puncturing a living body by the introducer assembly 10.

Accordingly, the tube member 160 including the thrombus inducing material M is indwelled in the introduction part P. For that reason, the thrombus inducing material M is indwelled in the introduction part P during a desired procedure. Accordingly, the formation of the thrombus in the introduction part P is promoted before the introducer sheath 100 is removed from the body lumen R. For that reason, it is possible to shorten a time necessary for hemostasis at the introduction part P after removing the introducer sheath 100 from the body lumen R.

In the step of performing the desired procedure, a treatment instrument such as a catheter or a guide wire is introduced into the body lumen R through the hemostatic valve 140 of the introducer sheath 100 while the introducer sheath 100 is indwelled in the body lumen R and, for example, a technique such as percutaneous transluminal coronary angioplasty (PTCA) is performed. Then, the treatment instrument introduced into the body lumen R is removed from the body lumen R after the technique ends.

In the step of removing the introducer sheath 100, the introducer sheath 100 is removed while the introduction part P is pressed so that the tube member 160 is pressed against the inner surface of the introduction part P and the thrombus inducing material M of the tube member 160 is applied to the inner surface of the introduction part P.

Accordingly, the formation of the thrombus at the introduction part P even after the introducer sheath 100 is removed from the body lumen R can be promoted. For this reason, it is possible to further shorten a time necessary for hemostasis at the introduction part P. Further, since the thrombus inducing material M is applied to the inner surface of the introduction part P, it is possible to effectively shorten a time necessary for hemostasis compared to, for example, a method of sticking a sheet material including a hemostasis agent to a skin.

After the introducer sheath 100 is removed from the body lumen R, hemostasis is performed by using a known hemostatic device.

According to the introducer sheath 100 of the embodiment, the thrombus inducing material M is disposed at the proximal side of the outer surface 117 of the catheter main body 110. Accordingly, the thrombus inducing material M can be indwelled at the introduction part P by inserting the proximal side of the catheter main body 110 into the introduction part P during a desired procedure. For that reason, the formation of the thrombus in the introduction part P before removing the introducer sheath 100 from the body lumen R can be promoted. Thus, it is possible to shorten a time necessary for hemostasis of the introduction part P at the time of performing hemostasis of the introduction part P by the hemostatic device after removing the introducer sheath 100 percutaneously introduced into the body lumen R from the body lumen R. For that reason, a physical burden on a patient can be reduced.

Further, according to the introducer sheath 100 of the embodiment, the tube member 160 including the thrombus inducing material M is disposed at the proximal side of the outer surface 117 of the catheter main body 110. For this reason, the outer diameter of the proximal portion provided with the thrombus inducing material M indwelled in the introduction part P increases by the thickness H2 of the tube member 160 while the outer diameter of the distal portion passing through the introduction part P in the introducer sheath 100 is maintained. Accordingly, the proximal portion provided with the thrombus inducing material M can adhere to the introduction part P while allowing the distal portion of the introducer sheath to pass through the introduction part P without excessively widening the introduction part P. For that reason, the introducer sheath 100 can prevent a positional deviation of a portion provided with the thrombus inducing material M in the introducer sheath 100 from the introduction part P without causing further bleeding at the introduction part P and can allow the thrombus inducing material M to further reliably contact the introduction part P. Thus, it is possible to more reliably shorten a time necessary for hemostasis of the introduction part P using the introducer sheath 100.

Further, the introducer sheath 100 of the embodiment further includes the strain relief 130, which covers the distal portion 121 of the hub 120 and surrounds a predetermined range of the proximal side of the catheter main body 110. Accordingly, the kink at the proximal side of the introducer sheath 100 when the introducer sheath 100 is introduced into the body lumen R can be prevented Thus, the operability of the introducer sheath 100 is improved.

Further, according to the introducer sheath 100 of the embodiment, the strain relief 130 covers a part of the tube member 160. Accordingly, the rigidity of the introducer sheath 100 gradually increases in order of the portion 110P1 only at the side of the catheter main body 110, the portion 110P2 provided with the tube member 160 in the catheter main body 110, and the portion 110P3 provided with the tube member 160 and the strain relief 130 in the catheter main body 110 in a direction from the distal side to the proximal side of the catheter main body 110. For that reason, the introducer sheath 100 can effectively prevent the kink at the proximal side. Thus, the operability of the introducer sheath 100 is further improved.

Further, according to the introducer sheath 100 of the embodiment, the thickness H2 of the tube member 160 is smaller than the thickness H1 of the catheter main body 110. Then, a material of the tube member 160 is harder than a material of the catheter main body 110. Accordingly, the rigidity of the tube member 160 can be increased without increasing the outer diameter of the portion provided with the tube member 160 in the introducer sheath 100 more than necessarily. Accordingly, the tube member 160 can be prevented from being separated toward the proximal side of the catheter main body 110 due to a resistance applied from the body tissue W to the distal side of the tube member 160 when the tube member 160 is introduced into the introduction part P. For that reason, the insertability of the introducer sheath 100 into the introduction part P is not damaged. Thus, the operability of the introducer sheath 100 is further improved.

Further, according to the introducer sheath 100 of the embodiment, the distal area S21 of the tube member 160 is inclined toward the outer surface 117 of the catheter main body 110. At the time of introducing the tube member 160 into the introduction part P, the distal area S21 first contacting the body tissue W in the tube member 160 receives a large resistance from the body tissue W. For that reason, since the distal area S21 of the tube member 160 is inclined toward the outer surface 117 of the catheter main body 110, a resistance applied from the body tissue W to the distal area S21 of the tube member 160 at the time of introducing the tube member 160 into the introduction part P can be reduced. For that reason, the insertability of the tube member 160 into the introduction part P can be improved. Thus, it is possible to more easily shorten a time necessary for hemostasis at the introduction part P using the introducer sheath 100.

Further, according to the introducer sheath 100 of the embodiment, a color of the tube member 160 is different from a color of the catheter main body 110. Accordingly, a range in which the thrombus inducing material M is disposed in the catheter main body 110 can more accurately be recognized. For that reason, the tube member 160 can be more reliably inserted into the introduction part P. Thus, it is possible to more reliably shorten a time necessary for hemostasis at the introduction part P using the introducer sheath 100.

Further, according to the introducer sheath 100 of the embodiment, the tube member 160 can include the main body portion 161 and the medicine portion 162, which is disposed on the outer surface 161a of the main body portion 161 and can include the thrombus inducing material M. Accordingly, since the tube member 160 is inserted into the introduction part P, the tube member 160 can allow the thrombus inducing material M to more reliably contact the introduction part P. Thus, it is possible to more reliably shorten a time necessary for hemostasis at the introduction part P using the introducer sheath 100.

Further, according to the introducer sheath 100 of the embodiment, the hydrophilic lubrication layer 170, which applies surface lubricity in a wet state is disposed on a part of the outer surface 117 of the catheter main body 110. Then, the tube member 160 is disposed on the area S1 of the catheter main body 110 without the hydrophilic lubrication layer 170. Accordingly, a relative slip between the catheter main body 110 and the tube member 160 through the hydrophilic lubrication layer 170 can be prevented. For that reason, a relative positional deviation between the catheter main body 110 and the tube member 160 when the tube member 160 is inserted into the introduction part P can be prevented. For that reason, the insertability of the tube member 160 into the introduction part P is improved. Thus, it is possible to more easily shorten a time necessary for hemostasis at the introduction part P using the introducer sheath 100.

Further, according to the introducer sheath 100 of the embodiment, the hydrophilic lubrication layer 170 covers at least the distal area S21 of the tube member 160. Accordingly, a resistance applied from the body tissue W to the distal area S21 of the tube member 160 when the tube member 160 is introduced into the introduction part P can be further reduced. For that reason, the insertability of the tube member 160 into the introduction part P is further improved. Thus, it is possible to more easily shorten a time necessary for hemostasis at the introduction part P using the introducer sheath 100.

In the above-described embodiment, the tube member 160 has a substantially cylindrical shape. However, a structure of the tube member is not particularly limited as long as the tube member can be disposed at the proximal side of the outer surface 117 of the catheter main body 110.

Figure 6:
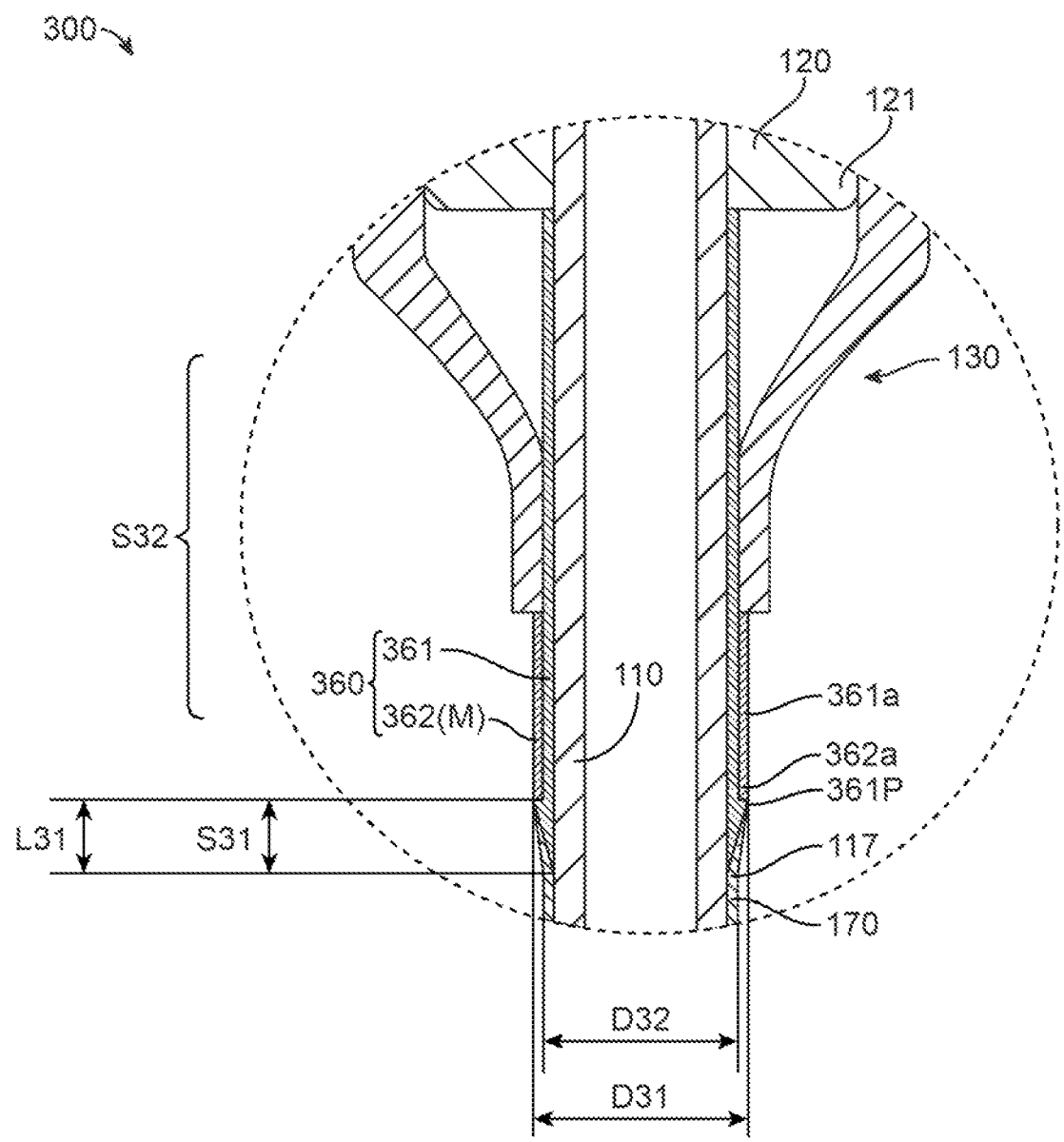
FIG. 6 is an enlarged cross-sectional view illustrating a main part of an introducer sheath according to a modified example and corresponding to FIG. 3A.

For example, in accordance with a modified example as illustrated in FIG. 6, a main body portion 361 of a tube member 360 can include a distal area S31 which is inclined toward the outer surface 117 of the catheter main body 110 and a proximal area S32 which is positioned at the proximal side in relation to the distal area S31 and an outer diameter D31 of a proximal end 361P of the distal area S31 may be larger than an outer diameter D32 of the proximal area S32. In this case, the medicine portion 362 is disposed on an outer surface 361a of the proximal area S32. Additionally, the distal area S31 is formed so that the outer periphery of the distal area S21 decreases from the proximal side to the distal side of the distal area S31.

For example, the outer diameter D32 of the proximal area S32 can be arbitrarily set to, for example, a range which is larger than 1 mm and is equal to or smaller than 4 mm. Then, the outer diameter D31 of the proximal end 361P of the distal area S31 can be arbitrarily set to, for example, a range which is larger than 1.1 mm and is equal to or smaller than 4.5 mm.

A length L31 of the distal area S31 is not particularly limited and can be arbitrarily set to, for example, a range of 0.1 mm to 10 mm.

The proximal area S32 contacts the distal portion 121 of the hub 120 and extends from the distal portion 121 of the hub 120 to the distal area S31 of the tube member 360. A length L32 of the proximal area S32 is not particularly limited and can be arbitrarily set to, for example, a range of 20 mm to 100 mm.

Note that the proximal portion of the main body portion 361 of the tube member 360 may extend to the proximal portion of the catheter main body 110. In that case, the proximal portion of the main body portion 361 of the tube member 360 or the proximal portion of the main body portion 361 of the tube member 360 and the proximal portion of the catheter main body 110 are fixed to the interlock portion of the hub 120.

Also in the introducer sheath 300 of the modified example, the treatment method is the same as that of the introducer sheath 100 according to the above-described first embodiment. For that reason, the introducer sheath 300 can shorten a time necessary for hemostasis at the introduction part P after removing the introducer sheath 300 from the body lumen R.

According to the introducer sheath 300 of the modified example, the main body portion 361 of the tube member 360 can include the distal area S31 which is inclined toward the outer surface 117 of the catheter main body 110 and the proximal area S32 which is positioned at the proximal side in relation to the distal area S31. At the time of introducing the tube member 360 into the introduction part P, the distal area S31 first contacting the body tissue W of the introduction part P in the tube member 360 receives a large resistance. For that reason, since the distal area S31 is inclined toward the outer surface 117 of the catheter main body 110, a resistance applied from the body tissue W to the distal area S31 of the tube member 360 when the tube member 360 is introduced into the introduction part P can be reduced. For that reason, the insertability of the tube member 360 into the introduction part P can be improved.

Further, according to the introducer sheath 300 of the modified example, the outer diameter D31 of the proximal end 361P of the distal area S31 is larger than the outer diameter D32 of the proximal area S32 and the thrombus inducing material M is disposed on the outer surface 361a of the proximal area S32. Accordingly, the thrombus inducing material M is disposed at a portion, which is recessed more than the proximal end 361P of the distal area S31 at the proximal side in relation to the distal area S31. For that reason, since the distal area S31 of the tube member 360 allows the body tissue W not to easily contact the distal portion 362a of the thrombus inducing material M when the tube member 360 is percutaneously introduced into the body lumen R, a resistance applied from the body tissue W of the introduction part P to the thrombus inducing material M can be reduced. As a result, the distal area S31 of the tube member 360 can prevent the thrombus inducing material M from being separated from the tube member 360. For that reason, it is possible to more reliably shorten a time necessary for hemostasis at the introduction part P using the introducer sheath 300.

As described above, the introducer sheath according to the disclosure has been described by the embodiment and the modified example thereof, but the disclosure is not limited to the above-described configurations and can be appropriately modified based on the description of claims.

For example, in the above-described embodiment and the modified example thereof, the thrombus inducing material M is disposed on the outer surface of the tube member. However, a method of arranging the thrombus inducing material M is not particularly limited as long as the tube member includes the thrombus inducing material M. For example, the thrombus inducing material M may be formed to be gradually released from the tube member.

Further, in the above-described embodiment and the modified example thereof, the tube member extends in the entire area surrounded by the strain relief in the outer surface of the catheter main body. However, the tube member may extend to only a part of the area surrounded by the strain relief in the outer surface of the catheter main body or may not extend to the area surrounded by the strain relief. However, in the introducer sheath, the strain relief desirably covers at least a part of the tube member from the viewpoint of kink resistance at the proximal side of the introducer sheath and the tube member more desirably extends in the entire area surrounded by the strain relief in the outer surface of the catheter main body.

Further, the introducer sheath may be provided with a cover member that covers the thrombus inducing material M in a separable manner. Accordingly, the cover member can prevent the thrombus inducing material M from contacting other objects during the transportation of the introducer sheath or before the desired procedure. For that reason, the introducer sheath including the cover member can prevent the thrombus inducing material M from being separated from the introducer sheath before the thrombus inducing material M is introduced into the introduction part P.

Furthermore, in the above-described embodiment and the modified example thereof, the hydrophilic lubrication layer is partially disposed on the outer surface of the catheter main body, but the hydrophilic lubrication layer may be disposed on the entire outer surface of the catheter main body. However, as described above, a structure in which the hydrophilic lubrication layer is partially disposed on the outer surface of the catheter main body are excellent due to the following reasons. That is, since the tube member is disposed on the area of the catheter main body without the hydrophilic lubrication layer, it is excellent in that the relative slip between the catheter main body and the tube member through the hydrophilic lubrication layer can be prevented.

The detailed description above describes an introducer sheath which is used in an introducer assembly corresponding to a medical instrument. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An introducer sheath comprising:
   a catheter main body configured to be percutaneously introduced into a body lumen;
   a hub configured to be connected to a proximal side of the catheter main body;
   a cylindrical tube member that includes a thrombus inducing material, and wherein the tube member is disposed at a proximal side of an outer surface of the catheter main body, the tube member including a main body portion and a medicine portion, the medicine portion being disposed on an outer surface of the main body portion and includes the thrombus inducing material, the main body portion includes a proximal area and a distal area, the distal area being inclined toward the outer surface of the catheter main body and the proximal area being positioned proximally to the distal area; and
   wherein an outer diameter of a proximal end of the distal area of the main body portion is larger than an outer diameter of the proximal area of the main body portion.

2. The introducer sheath according to claim 1,
   wherein a thickness of the tube member is smaller than a thickness of the catheter main body; and
   wherein a material of the tube member is harder than a material of the catheter main body.

3. The introducer sheath according to claim 1,
   wherein a distal area of the tube member is inclined toward the outer surface of the catheter main body.

4. The introducer sheath according to claim 1,
   wherein a color of the tube member is different from a color of the catheter main body.

5. The introducer sheath according to claim 1,
   wherein the medicine portion is disposed on an outer surface of the proximal area.

6. The introducer sheath according to claim 1,
   wherein a hydrophilic lubrication layer which exhibits surface lubricity in a wet state is partially disposed on the outer surface of the catheter main body; and
   wherein the tube member is disposed in an area of the catheter main body without the hydrophilic lubrication layer.

7. The introducer sheath according to claim 1, wherein a proximal portion of the main body portion of the tube member extends to a proximal portion of the catheter main body.

8. The introducer sheath according to claim 7, wherein the hub includes an interlock portion, and the proximal portion of the main body portion of the tube member is fixed to the interlock portion of the hub, or the proximal portion of the main body portion of the tube member and the proximal portion of the catheter main body are fixed to the interlock portion of the hub.

9. The introducer sheath according to claim 1, wherein a proximal portion of the main body portion of the tube member contacts a distal portion of the hub.

10. The introducer sheath according to claim 1, wherein the medicine portion is disposed around an entire circumference of the outer surface of the main body portion of the tube member.

11. The introducer sheath according to claim 1, wherein the thrombus inducing material is a collagen or high molecular weight vWF factor.

12. An introducer sheath comprising:
    a catheter main body configured to be percutaneously introduced into a body lumen;
    a hub configured to be connected to a proximal side of the catheter main body;
    a cylindrical tube member that includes a thrombus inducing material, and wherein the tube member is disposed at a proximal side of an outer surface of the catheter main body, the tube member including a main body portion and a medicine portion, the medicine portion being disposed on an outer surface of the main body portion and includes the thrombus inducing material;

wherein a hydrophilic lubrication layer which exhibits surface lubricity in a wet state is disposed on the outer surface of the catheter main body; and wherein the hydrophilic lubrication layer covers at least a distal area of the tube member.

13. The introducer sheath according to claim 12, wherein the main body portion includes a proximal area and a distal area, the distal area being inclined toward the outer surface of the catheter main body and the proximal area being positioned proximally to the distal area.

14. The introducer sheath according to claim 13, wherein an outer diameter of a proximal end of the distal area of the main body portion is larger than an outer diameter of the proximal area of the main body portion.

15. The introducer sheath according to claim 12, wherein the medicine portion is disposed on an outer surface of a proximal area of the main body portion.

16. The introducer sheath according to claim 12,
wherein a thickness of the tube member is smaller than a thickness of the catheter main body; and
wherein a material of the tube member is harder than a material of the catheter main body.

17. The introducer sheath according to claim 12,
wherein a distal area of the tube member is inclined toward the outer surface of the catheter main body.

18. The introducer sheath according to claim 12,
wherein a color of the tube member is different from a color of the catheter main body.

19. The introducer sheath according to claim 12, wherein a proximal portion of the main body portion of the tube member extends to a proximal portion of the catheter main body; and wherein the hub includes an interlock portion, and the proximal portion of the main body portion of the tube member is fixed to the interlock portion of the hub, or the proximal portion of the main body portion of the tube member and the proximal portion of the catheter main body are fixed to the interlock portion of the hub.

20. An introducer sheath comprising:
a catheter main body configured to be percutaneously introduced into a body lumen;
a hub configured to be connected to a proximal side of the catheter main body;
a cylindrical tube member that includes a thrombus inducing material, and wherein the tube member is disposed at a proximal side of an outer surface of the catheter main body, the tube member including a main body portion and a medicine portion, the medicine portion being disposed on an outer surface of the main body portion and includes the thrombus inducing material; and wherein the catheter main body is made of polyethylene or polypropylene, and the tube member is made of polycarbonate and polyether ether ketone (PEEK).

* * * * *